(12) United States Patent
Padilla Arias et al.

(10) Patent No.: US 10,182,959 B2
(45) Date of Patent: Jan. 22, 2019

(54) SPATIAL SENSING DEVICE

(71) Applicant: ENAAY TECNOLOGÍAS SA DE CV, Zapopan, Jalisco (MX)

(72) Inventors: Cuauthli Padilla Arias, Jalisco (MX); Marco Antonio Trujillo Tejeda, Jalisco (MX)

(73) Assignee: ENAAY TECNOLOGÍAS SA DE CV, Zapopan, Jalisco (MX)

( * ) Notice: Subject to any disclaimer, the term of this patent is extended or adjusted under 35 U.S.C. 154(b) by 465 days.

(21) Appl. No.: 14/787,509

(22) PCT Filed: Jul. 23, 2015

(86) PCT No.: PCT/IB2015/055588
§ 371 (c)(1),
(2) Date: Oct. 28, 2015

(87) PCT Pub. No.: WO2017/013473
PCT Pub. Date: Jan. 26, 2017

(65) Prior Publication Data
US 2017/0156964 A1    Jun. 8, 2017

(51) Int. Cl.
*A61H 3/06* (2006.01)
*B06B 1/06* (2006.01)
(Continued)

(52) U.S. Cl.
CPC .............. *A61H 3/061* (2013.01); *B06B 1/06* (2013.01); *G01S 7/521* (2013.01); *G01S 15/42* (2013.01);
(Continued)

(58) Field of Classification Search
CPC .............. A61H 3/061; A61H 2003/007; A61H 2003/063; A61H 2201/50;
(Continued)

(56) References Cited

U.S. PATENT DOCUMENTS 3,172,075 A * 3/1965 Kay ..................... G01S 15/34
342/24
3,987,403 A    10/1976 Smith
(Continued)

FOREIGN PATENT DOCUMENTS

CN    102048612 A    5/2011
CN    102614068 A    8/2012
(Continued)

OTHER PUBLICATIONS

Guía pulsera 'murciélago' a ciegos_Noticiasnet Dec. 7, 2014; http://old.nvinoticias.com/oaxaca/vida/salud/249294-guia-pulsera-murcielago-ciegos. (Year: 2014).*
(Continued)

*Primary Examiner* — Daniel Pihulic
(74) *Attorney, Agent, or Firm* — Browdy and Neimark, PLLC

(57) ABSTRACT

A spatial sensing device to improve the user's movement ability and provide assistance in the autonomous walking of visually impaired or blind people, which is also easy-to-use, ergonomic and portable, the device comprises a housing including a set of modules; attaching means bonded to the housing in order to secure the device to the user; at least one user information access means; and an ultrasound transducer positioned at the junction between one housing side and the attaching means; the device is characterized in that the ultrasound transducer is positioned on the device at a slant angle (α) with respect to the device axis (Z), such that during the use of the device, the ultrasound transducer is directed toward the user's front side in order to emit and detect signals which will be processed by the set of modules in the housing, wherein the set of modules comprises a processing module interacting with an intercommunication module, a
(Continued)

position and/or movement sensing module, a spatial sensing module, and a power module.

27 Claims, 5 Drawing Sheets

(51) Int. Cl.
| | | |
|---|---|---|
| *G01S 7/521* | (2006.01) | |
| *G01S 15/42* | (2006.01) | |
| *G01S 15/93* | (2006.01) | |
| *G06F 19/00* | (2018.01) | |
| *G16H 40/63* | (2018.01) | |
| *A61H 3/00* | (2006.01) | |

(52) U.S. Cl.
CPC ............. *G01S 15/93* (2013.01); *G06F 19/00* (2013.01); *G16H 40/63* (2018.01); *A61H 2003/007* (2013.01); *A61H 2003/063* (2013.01); *A61H 2201/165* (2013.01); *A61H 2201/1635* (2013.01); *A61H 2201/50* (2013.01); *A61H 2201/5048* (2013.01); *A61H 2201/5058* (2013.01); *A61H 2201/5064* (2013.01); *A61H 2201/5079* (2013.01); *A61H 2201/5084* (2013.01); *A61H 2201/5097* (2013.01)

(58) Field of Classification Search
CPC ...... A61H 2201/165; A61H 2201/5097; A61H 2201/5084; A61H 2201/5079; A61H 2201/5064; A61H 2201/5058; A61H 2201/5048; A61H 2201/1635; G01S 15/93; G01S 15/42; G01S 7/521; B06B 1/06; G16H 40/63; G06F 19/00
See application file for complete search history.

(56) References Cited

U.S. PATENT DOCUMENTS

| | | | | |
|---|---|---|---|---|
| 5,724,313 | A * | 3/1998 | Burgess | A61H 3/061 367/102 |
| 6,011,754 | A * | 1/2000 | Burgess | A61H 3/061 367/102 |
| 6,469,956 | B1 * | 10/2002 | Zeng | G01S 7/521 367/116 |
| 6,671,226 | B1 * | 12/2003 | Finkel | A61H 3/061 367/116 |
| 7,054,246 | B2 | 5/2006 | Ueno | |
| 7,957,224 | B2 * | 6/2011 | Tremper | G01S 7/52003 367/116 |
| 9,183,708 | B2 * | 11/2015 | Daeef | G08B 3/10 |
| 9,377,530 | B2 * | 6/2016 | Kish | A61H 3/061 |
| 2014/0269189 | A1 * | 9/2014 | Kish | A61H 3/061 367/87 |
| 2017/0156964 | A1 * | 6/2017 | Padilla Arias | A61H 3/061 |

FOREIGN PATENT DOCUMENTS

| | | | |
|---|---|---|---|
| CN | 103312899 A | | 9/2013 |
| DE | 3544047 A1 | | 6/1987 |
| DE | 3836961 A1 | | 5/1990 |
| GB | 2448166 | * | 10/2008 |
| JP | 1091582 A | | 5/1986 |
| WO | 2012159128 A2 | | 11/2012 |
| WO | WO-2017013473 A1 | * | 1/2017 ............... A61H 3/06 |

OTHER PUBLICATIONS

Translation of application No. PCT/IB2015/05588 form 237 publication No. WO2017013473, (Year: 2017).*

* cited by examiner

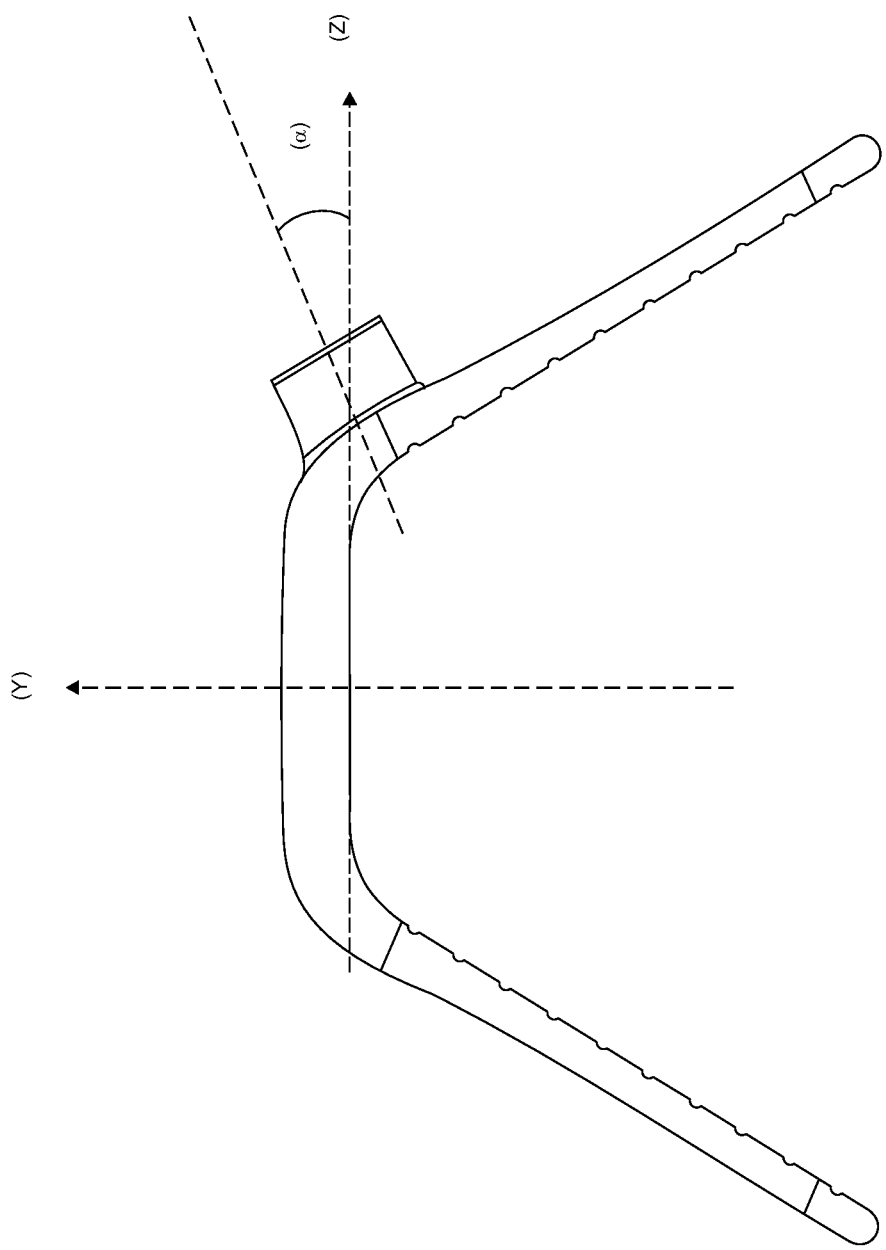
FIG. 1-A

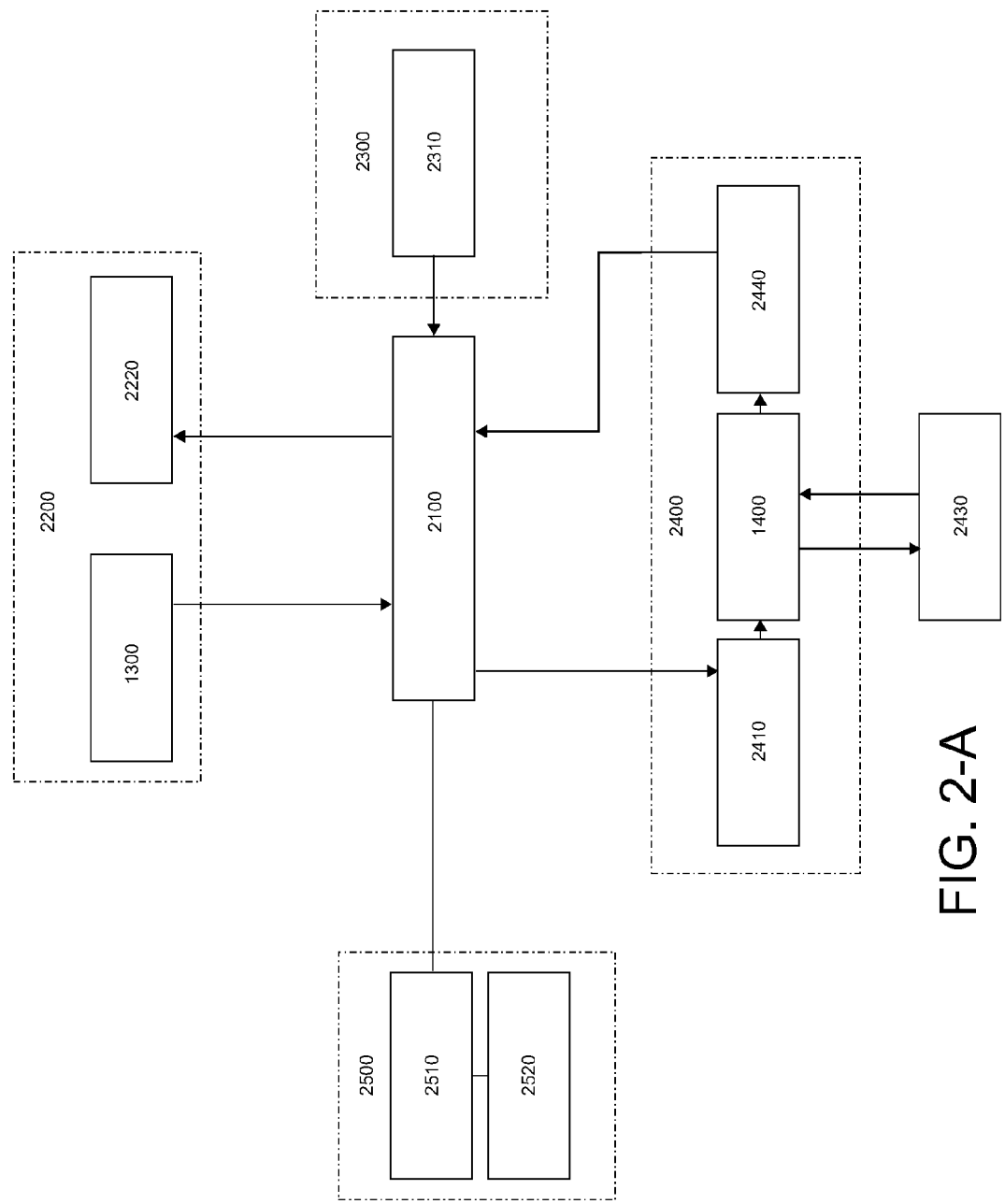
FIG. 2-A

SPATIAL SENSING DEVICE

TECHNICAL FIELD

This invention is related to techniques to aid visually impaired or blind people's mobility, and more particularly, it is related to spatial sensing devices to improve personal movement and walking abilities.

BACKGROUND OF THE INVENTION

As it is known, one of the main difficulties visually impaired or blind people have to face is being able to interact in changing and/or unknown environments, since this involves the existence of several obstacles and difficulties impeding their free-movement.

Currently, there are different solutions to aid visually impaired or blind people, including "white" canes, specially trained dogs, or even electronic devices comprising video systems, ultrasound sensing systems, laser-based systems, echolocation-based systems having microphones and transducers, and GPS navigation systems through smart devices.

The use of different media to aid visually impaired or blind people depends on the users' ability to utilize said media, as well as on the cost thereof.

The so-called "white" canes are instruments which allow identifying that a person is visually impaired or blind; further, these instruments allow them to move autonomously. This tactile tool guides blind people's paces by helping them sense the type of surface they are walking on, as well as the obstacles that might be in their way; however, said white cane offers a sensing capability only below the user's waist, which allows to walk sensing surfaces and obstacles at a short distance, but leaving the user unaware of suspended or projecting objects at a higher height, such as tree branches, extinguishers, vending machines, vehicle and trucks rear-view mirrors, cantilevers or furniture projecting edges, among others.

Nowadays, there are devices having the purpose of helping to reduce said white-cane limitations, which comprise bayed canes to help blind people, said canes have additional devices using laser rays or ultrasound devices which function is sensing a single object at a time, which is located at a specific height with respect to the user, that is to say, to be located in front of the user, at the user's head level or at ground level.

Said canes having additional devices need to be configured by the user in order to carry out the sensing of the object, according to the height needed to be recorded, and they could be very expensive or they might fail at sensing all the obstacles being present to the user, thus limiting his/her movements. In addition, these canes, when not in use, need to be disassembled and carried, either in special containers or in any other kind of cane-carrier, thus implying the disadvantage of said white canes getting lost easily.

In addition, there are other multiple electronic devices such as support instruments for the visually impaired or blind, however, these are expensive and impractical. For example, there are belts having sensors and comprising a big-sized and heavy-weight controller, and due to said features, said controllers have to be carried on a special compartment on the user's back.

Particularly, in the state of the art, U.S. Pat. No. 4,280,204 was found, related to a cane having an ultrasound sensor that feeds back the user by a sound emission, which causes interference with other existing aid elements for the visually impaired or blind, either in walkways or in facilities having this kind of aids which also emit warning sounds to the user.

U.S. Pat. No. 7,054,246 relates to an electronic device, serving as a support for the visually impaired or blind, by using an Echolocation system; said device has the drawback of being non-easily adaptable to the user, i.e., it is non-ergonomic, non-portable and it has a great volume.

DE3836961 shows an orientation device for blind people, using an ultrasound sensor, but said device is non-ergonomic or comfortable to the user.

Likewise, DE3544047 describes the use of the same ultrasound sensor system adapted to a white cane.

JP61091582 relates to a radar principle-based method and system; however, its implementation is extremely expensive.

U.S. Pat. No. 3,987,403 makes reference to a radar system using one transmitter and two ultrasound receivers, which has the disadvantage of specially requiring a reference or transmitter to be able to move from one location to another.

CN103312899 discloses an application to be installed in a smart-phone, whereby the photographic camera module in said phone works as a guide for blind people; however, it has the obvious disadvantage of requiring the use of a smart-phone, and further, most smart-phones comprise an interaction medium with the user such as a touch-screen, which is obviously difficult to manage by a visually impaired or blind person, and this limits the user by having to get a smart-phone specially designed for visually impaired or blind people.

WO2012159128 discloses a device having two or more components, where one is attached to a white cane and the other components are attached to different user's body parts. This has clear disadvantages due to its complex utilization.

CN102614068 discloses a complex companion-robot system for the visually impaired or blind, which communicates with the user by means of a waist-cord, which in turn supports another warning sign-emitting device. This system, as may be seen in said document, is complex, it comprises several spaced apart elements and consequently multiple connections, and further, it is extremely expensive.

CN102048612 discloses a robotic-vehicle, which records the environment by means of a camera, processes it and communicates it to the user, this device has the clear disadvantage of being expensive added to the complex operation thereof.

In view of the above, the intention is to overcome the drawbacks and disadvantages present in the devices of the state of the art in order to help the visually impaired or blind to move, by means of a new electronic device allowing to detect the user surrounding environment making it easier for him/her to move, as well as to offer an easy-to-use, low-cost ergonomic portable device.

OBJECTS OF THE INVENTION

Taking into account the inconveniences and drawbacks of the prior art, it is an object of the present invention to provide a spatial sensing device to improve the movement and walking abilities of visually impaired or blind people.

It is another object of the present invention to provide a spatial sensing device allowing to detect objects at different distances and heights in front of a user.

It is an additional object of the present invention to provide a spatial sensing device preventing the interference from other close similar devices.

It is a further object of the present invention to provide an easy-to-use, low-cost ergonomic portable device to be used by a visually impaired or blind person.

These and other objects are attained by means of a spatial sensing device in accordance to the present invention.

SUMMARY OF THE INVENTION

The present invention solves the problems and disadvantages present in the state of the art by providing a spatial sensing device comprising: a housing including a set of modules; attaching means bonded to the housing in order to secure the device to the user; at least one user information access means; and an ultrasound transducer positioned at the junction between one housing side and the attaching means; the device is characterized in that the ultrasound transducer is positioned on the device at a slant angle (α) with respect to the device axis (Z), such that during the use of the device, the ultrasound transducer is directed toward the user's front side in order to emit and detect signals which will be processed by the set of modules in the housing, wherein the set of modules comprises a processing module interacting with an intercommunication module, a position and/or movement sensing module, a spatial sensing module, and a power module.

BRIEF DESCRIPTION OF THE DRAWINGS

The novel aspects considered characteristic of the present invention will be particularly established in the appended claims. However, the operation together with other objects and advantages thereof, will be better understood from the following detailed description of the invention, when read related to the appended drawings, wherein:

FIG. 1A is a left side view of the spatial sensing device of the present invention.

FIG. 2A is a block diagram specifically showing the components of each module in FIG. 2

DETAILED DESCRIPTION OF THE INVENTION

The present invention relates to a spatial sensing device to improve the user's movement ability, and to provide aid in the autonomous movement of visually impaired or blind people, which is also easy-to-use, ergonomic and portable.

Figure 1:
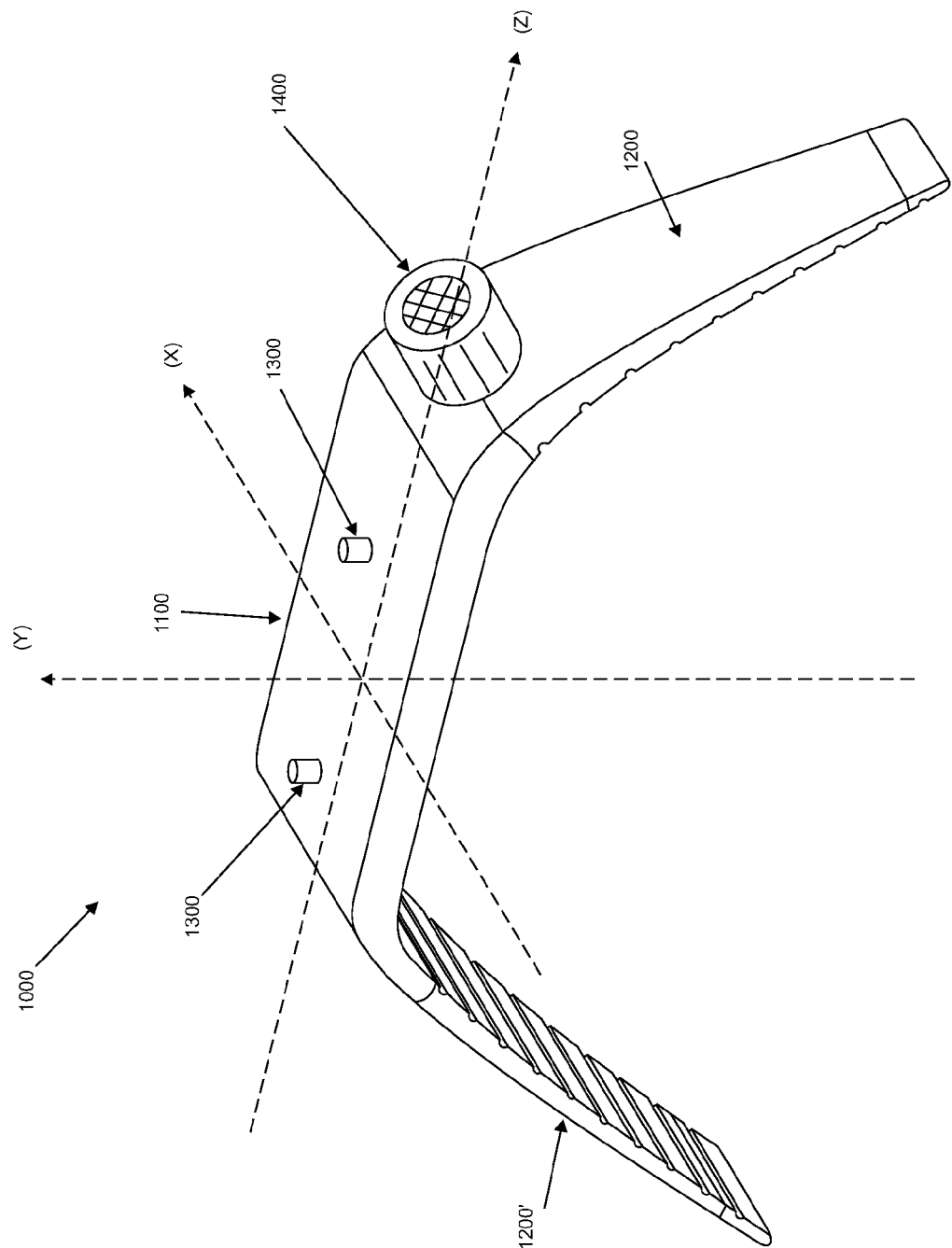
FIG. 1 is a perspective view of an embodiment of the spatial sensing device of the present invention.

FIG. 1 shows the spatial sensing device (1000) comprising: a housing (1100) including a set of modules for processing the signals; attaching means (1200, 1200') bonded to the housing in order to secure the device to the user; user information access means (1300); and an ultrasound transducer (1400) positioned at the junction between one housing side (1100) and the attaching means (1200); similarly, the axes (X), (Y), and (Z) of the spatial sensing device (1000) are illustrated; the device is characterized in that the ultrasound transducer (1400) is positioned on the device at a slant angle (α) with respect to the device axis (Z), such that when using the device the ultrasound transducer is directed toward the user's front side in order to emit and detect signals which will be processed by the set of modules in the housing, wherein the set of modules comprises: a processing module interacting with an intercommunication module, a position and/or movement sensing module, a spatial sensing module, and a power module (not shown in FIG. 1).

The spatial sensing device (1000) according to the present invention is easy-to-use and portable, preferably to be carried by the user's arms, more preferably, to be used at the distal end of any of the user's forearms.

In a preferred embodiment of the present invention, the attaching means (1200, 1200') are bonded by one end at each housing sides (1100) and are bonded at the other end to each other to secure the device to the user.

The attaching means (1200, 1200') are not limited regarding the type of bonding between said attaching means and the housing, as well as therebetween to secure the device to the user, any kind of bonding can be used. The user information access means (1300) relates mainly to devices of the type comprising, among others, the switch type, more specifically, those including buttons and/or tactile sensors, which through a certain number of keystrokes or a combination thereof by the user, the operation mode of the device is selected, i.e., if the user wishes to detect objects (2430) either above or at the user's head height, or in front of the user or at the ground level, or if there are slops on the surface the user is walking on.

The ultrasound transducer (1400) is selected from piezoelectric transducers and must be located at the juncture between the housing (1100) and the attaching means (1200), such that when the user is using the device, said ultrasound transducer be directed toward the user's front side in order to emit and detect signals to be processed, and which will help to detect and avoid obstacles in the user's path.

The signals emitted and sensed by the ultrasound transducer (1400) will be processed by a set of modules for the signal processing and sensing.

FIG. 1A shows a left side upper view of the spatial sensing device (1000) wherein the device axes (Y) and (Z) are illustrated as well as angle (α) in which the ultrasound transducer (1400) is slanted, said ultrasound transducer (1401) emits the signal, said angle (α) is located at a range between 20° and 35° with respect to the axis (Z), and more specifically between 25° and 30°.

Figure 2:
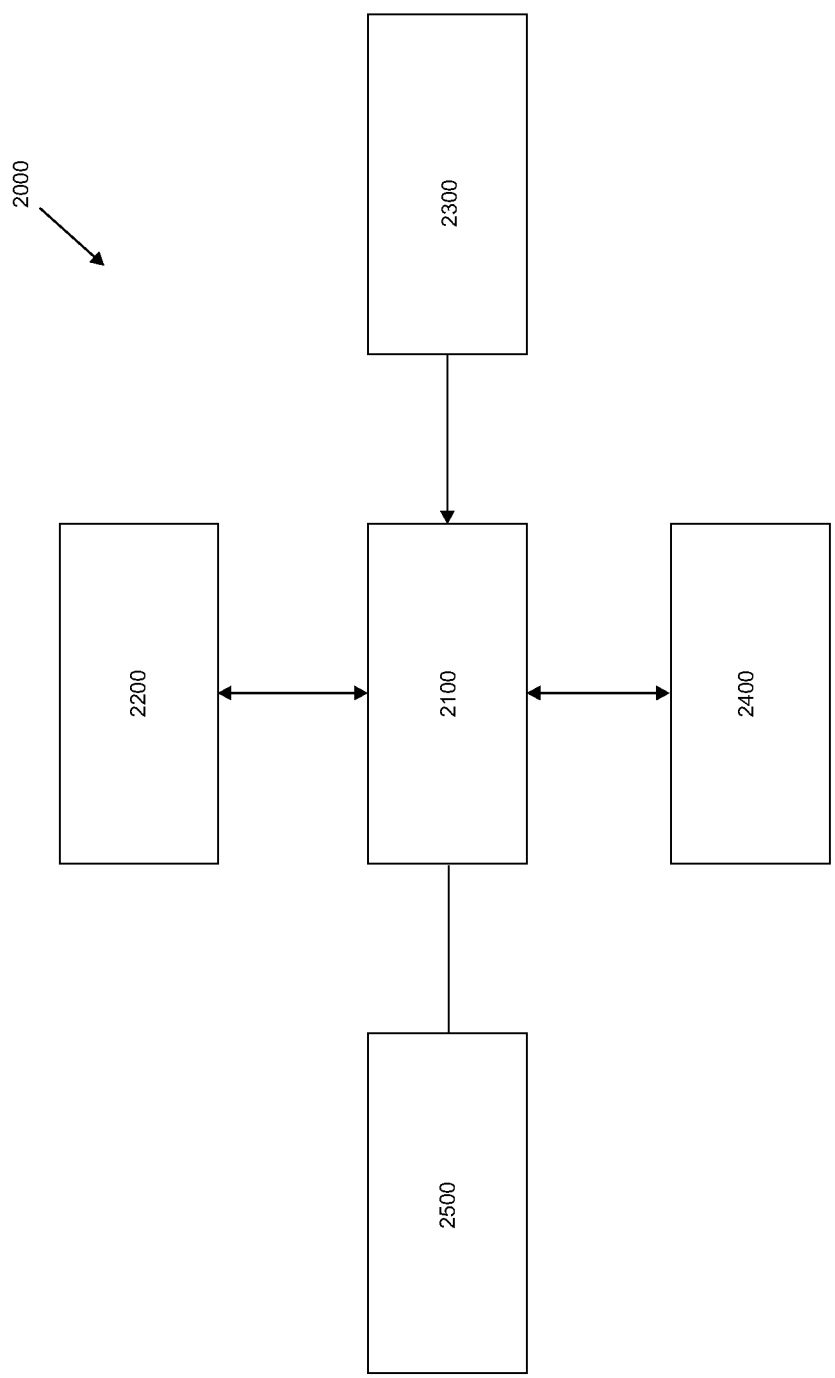
FIG. 2 is a block diagram of the set of modules of the spatial sensing device of the present invention.

FIG. 2 shows in general a block diagram of the set of modules (2000) included in the housing (1100), comprising a processing module (2100) interacting with an intercommunication module (2200), a position and/or movement sensing module (2300), a spatial sensing module (2400) and a power module (2500).

Referring to FIG. 2A, a block diagram is illustrated in detail including each element conforming each signal processing and sensing module (2000) in FIG. 2, wherein the processing module (2100) receives and sends signals to the other modules for the device operation.

When the device is turned on, the intercommunication module (2200) is actuated by the user through the user information access means (1300), which sends a signal to the processing module (2100) in order to activate the device as well as the user's desired mode of operation of the device.

This intercommunication module (2200), besides comprising the user information access means, also includes user warning means (2220), which informs the user, either by an audio signal, a vibration or other signal capable of being detected by the person, when an object (2430) is located in front of him/her.

Once the device is activated, the position and/or movement sensing module (2300) sends signals to the processing module (2100) relative to the position and/or movement of the device, thereby causing the processing module (2100) to send a first output signal to the spatial sensing module (2400).

The position and/or movement sensing module (2300), detects the device position when carried by the user, as well as if the user is in motion, and in this way it determines the direction to which the signal will be emitted from the ultrasound transducer (1400) in order to detect objects (2430) or obstacles in the walking path.

Said position and/or movement sensing module (2300) is selected from sensors of the type comprising: position detecting sensors, slope sensors, diversion sensors, as well as speed detecting sensors, preferably, it comprises sensors of the type comprising accelerometers, gyroscopes and/or mercury sensors, among others.

The spatial sensing module (2400) includes at least an output voltage variable-amplification means (2410), an ultrasound transducer (1400), and at least input voltage variable-amplification means (2440); where said spatial sensing module (2400) receives signals from the processing module (2100).

The output voltage variable-amplification means (2410) receives said first output signal from the processing module (2100) and amplifies or decreases the voltage in said electrical signal according to the operation mode of the device selected by the user, and according to the position and/or movement detected by the position and/or movement sensing module (2300); the amplified or diminished signal is sent to the ultrasound transducer (1400) to be converted into an ultrasound signal and to be emitted.

This signal emitted, will produce an echo when finding some element in the user movement path, and it will be detected by the same ultrasound transducer (1400) which will convert the ultrasound signal into an electrical signal detected to be sent to the at least one input variable voltage amplification medium (2440).

The at least one input voltage variable-amplification means (2440) receives said detected electrical signal from the ultrasound transducer (1400) and amplifies or decreases the voltage of the detected electrical signal according to the operation mode of the device selected by the user, and according to the position and/or motion detected by the position and/or movement sensing module (2300); said signal is sent to the processing module (2100).

This signal received at the processing module (2100), is sent to the intercommunication module (2200), specifically to the user warning media (2220), which will generate an audio signal, a vibration, or any other signal warning the user that there is an object or an obstacle (2430) in the movement path.

All of the modules described above operate using the power module (2500), which includes energy storing means (2510) and wireless energy recharging media (2520) providing the necessary energy for proper operation thereof, the wireless energy recharging means mainly relates to devices including, among others, the magnetic induction-type, more specifically, those comprising the Qi protocol.

Moreover, the input and output voltage variable-amplification means (2410, 2440), are selected from the type including voltage amplifiers that either increase or decrease the voltage of the electrical signal, according to the operation mode selected by the user, and also to the position and/or movement detected by the position and/or movement sensing module (2300), wherein said voltage increase or decrease causes the ultrasound transducer to have greater sensitivity and be able to locate objects within a distance in the range between 0.1 m and 6 m.

As a consequence, the ultrasound transducer, by receiving the voltage increased or decreased signal, is able to modify the amplitude of the operation vibration or frequency being generated, in order to detect said objects (2430) in front of the user or subject wearing the spatial sensing device, either on the walking surface, at different distances and/or at different heights.

In a preferred embodiment, the space sensing device of the present invention avoids the operation interference with another space sensing device, by identifying the signals through a communication system comprising at least a wireless communication system, selected from wi-fi, bluetooth, or any other RF signal emitted by both devices.

To avoid interference between similar devices, the devices coordinate the emission of the ultrasound transducer signals, such that alternate signals are generated in each transducer.

Figure 3:
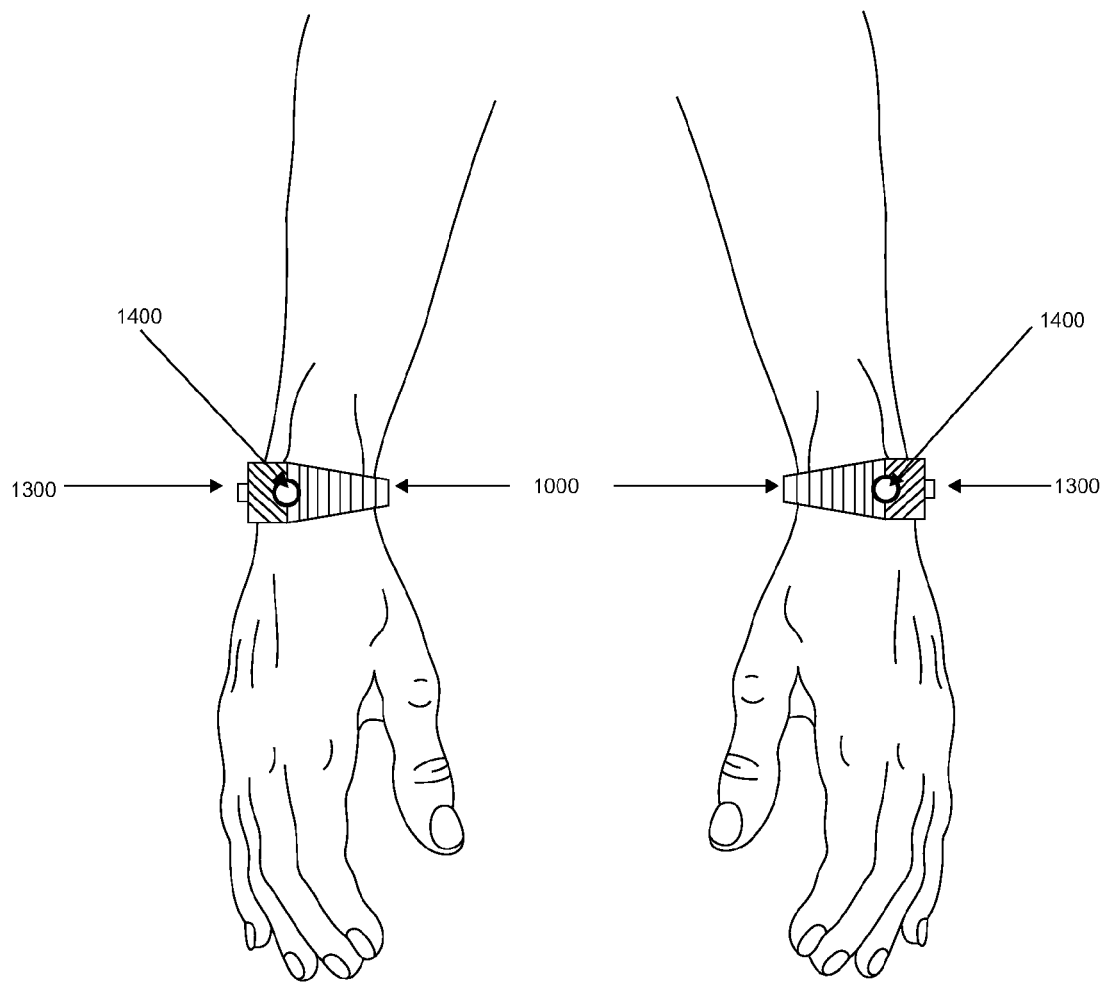
FIG. 3 shows the spatial sensing device of the present invention carried by a user.

FIG. 3 shows how the spatial sensing device (1000) should be worn by the user, illustrating the specific location of the ultrasound transducer (1400), with the purpose of properly emitting and detecting the signals, in order to determine if there are obstacles in front of the user, and thus, once the warning signal is generated, the user may modify the walking path, avoiding a collision with the objects (2430) in front of him/her.

According to the above-described, it will be apparent to the skilled in the art that the embodiments of the spatial sensing device above described and illustrated are shown for illustrative purposes only, as a person skilled in the art can perform several variations thereto, for example, varying the position of the ultrasound device, or using different sensing means for the user's position or movement. Accordingly, the present invention includes all the embodiments a person skilled in the art may envision from the concepts comprised in the present description.

The invention claimed is:

1. A spatial sensing device comprising: a housing including a set of modules; attaching means bonded to the housing to secure the device to a user; at least one user information access means; and an ultrasound transducer; wherein the ultrasound transducer is located in the device at a slant angle (a) with respect to the device axis (Z), such that when using the device, the ultrasound transducer is directed toward the user's front side in order to emit and detect signals which are to be processed by the set of modules in the housing, wherein the set of modules comprises: a processor module interacting with an intercommunication module, a position and/or movement sensing module, a spatial sensor module, and a power module; wherein the position and/or movement sensing module is selected from sensors of the type comprising: position detecting sensors, slope sensors, diversion sensors, and speed detecting sensors.

2. The device according to claim 1, wherein the ultrasound transducer is located at the junction between the housing and the attaching means.

3. The device according to claim 1, wherein the attaching means are bonded by one end to each side of the housing, and are bonded at the other end to each other in order to secure the device to the user.

4. The device according to claim 1, wherein the user information access means is selected from switch-type devices, more specifically, those comprising buttons and/or touch sensors.

5. The device according to claim 1, wherein through a certain number of keystrokes on the user information access means, or a combination thereof by the user in case the device comprises more than one user information access means, the desired operation mode of the device is determined.

6. The device according to claim 5, wherein the desired operation mode of the device comprises sensing the objects above or at the user's height, in front of the user or at ground level, as well as if there is any slope on the surface the user is walking on.

7. The device according to claim 1, wherein the ultrasound transducer is selected from piezoelectric-type transducers.

8. The device according to claim 1, wherein the angle ($\alpha$) at which the ultrasound transducer is slanted and at which the ultrasound transducer signal is emitted, is located in a range with respect to the axis (Z) between 20° and 35°.

9. The device according to claim 8, wherein the angle ($\alpha$) is located preferably in a range with respect to the axis (Z) between 25° and 30°.

10. The device according to claim 1, wherein the intercommunication module is actuated by the user through the user information access means, which sends a signal to the processor module to activate the device, as well as to select an operation mode of the device.

11. The device according to claim 1, wherein said intercommunication module further comprises user warning means.

12. The device according to claim 1, wherein the position and/or movement sensing module sends signals to the processor module relative to the position and/or movement of the device, causing said processor module to send a first output signal to the spatial sensor module.

13. The device according to claim 1, wherein the position and/or movement sensing module detects the position in which the device is located when worn by the user, as well as its movement.

14. The device according to claim 1, wherein the position and/or movement sensing module is preferably selected from sensors of the type comprising accelerometers, gyroscopes and/or mercury sensors.

15. The device according to claim 1, wherein the spatial sensor module includes at least one output voltage variable-amplification means, the ultrasound transducer, and at least one input voltage variable-amplification means.

16. The device according to claim 15, wherein the output voltage variable-amplification means receives a first output signal from the processor module and amplifies or decreases the voltage in said first output signal according to the operation mode of the device selected by the user, and according to the position and/or movement detected by the position and/or movement sensing module.

17. The device according to claim 16, wherein the amplified or reduced signal is sent to the ultrasound transducer to convert it into an ultrasound signal to be emitted.

18. The device according to claim 17, wherein the emitted signal will produce an echo when finding any element in the user's walking path, and it will be detected by the same ultrasound transducer which will convert the ultrasound signal into a detected electrical signal to send it to the input voltage variable-amplification means.

19. The device according to claim 15, wherein the input voltage variable-amplification means receives said detected electrical signal from the ultrasound transducer, and amplifies or decreases the voltage of the electrical signal detected according to the operation mode of the device selected by the user, and according to the position and/or movement detected by the position and/or movement sensing module; said signal is sent to the processor module.

20. The device according to claim 19, wherein the signal received by the processor module is sent to the intercommunication module, specifically to the user warning means, which will generate an audio signal, a vibration, or any other signal warning the user of an existing object or obstacle in the walking path.

21. The device according to claim 1, wherein the set of modules operates through the power module, which includes energy storage means and energy wireless recharging means.

22. The device according to claim 21, wherein the wireless energy recharging means comprises, among others, the magnetic induction type, more specifically, those which comprise the Qi protocol.

23. The device according to claim 15, wherein the input and output voltage variable-amplification means are selected from the type comprising voltage amplifiers increasing or decreasing the electrical signal voltage, according to the operation mode selected by the user, and also according to the position and/or movement detected by the position and/or movement sensing module.

24. The device according to claim 23, wherein said voltage increase or decrease causes the ultrasound transducer to have greater sensitivity and to be able to locate objects within a distance in the range between 0.1 m and 6 m.

25. The device according to claim 1, comprising a communication system to avoid operation interference with another similar device.

26. The device according to claim 25, wherein the communication system comprises at least a wireless communication system selected from wi-fi, bluetooth, or any other radio frequency signal being emitted by both devices.

27. The device according to claim 25, wherein the communication system coordinates the signal emission from the ultrasound transducers of different devices, such that alternate signals are generated from each transducer.

* * * * *